United States Patent [19]

Stockel et al.

[11] Patent Number: 4,654,208

[45] Date of Patent: * Mar. 31, 1987

[54] ANTI-MICROBIAL COMPOSITIONS COMPRISING AN AQUEOUS SOLUTION OF A GERMICIDAL POLYMERIC NITROGEN COMPOUND AND A POTENTIATING OXIDIZING AGENT

[76] Inventors: Richard F. Stockel, 475 Rolling Hills Rd., Bridgewater, N.J. 08807; Murray Jelling, 21 Spring Hill Rd., Roslyn Heights, N.Y. 11577

[*] Notice: The portion of the term of this patent subsequent to Feb. 12, 2002 has been disclaimed.

[21] Appl. No.: 700,745

[22] Filed: Feb. 12, 1985

Related U.S. Application Data

[63] Continuation-in-part of Ser. No. 471,011, Mar. 1, 1983, Pat. No. 4,499,077, which is a continuation of Ser. No. 231,257, Feb. 3, 1981, abandoned.

[51] Int. Cl.$^4$ .................... A01N 43/58; A01N 37/52; A01N 33/12; A61K 31/74
[52] U.S. Cl. ................................. 424/78; 514/252; 514/635; 514/642
[58] Field of Search ................ 514/635, 642, 252; 424/78

[56] References Cited

U.S. PATENT DOCUMENTS

| | | | |
|---|---|---|---|
| 2,917,428 | 12/1959 | Hitzman | 424/130 |
| 3,123,521 | 3/1964 | Wentworth et al. | 424/130 |
| 3,689,673 | 9/1972 | Phares | 424/326 |
| 4,026,945 | 5/1977 | Green et al. | 424/78 |
| 4,029,817 | 6/1977 | Blanco et al. | 424/80 |
| 4,073,888 | 2/1978 | Snyder | 424/149 |

*Primary Examiner*—Douglas W. Robinson
*Attorney, Agent, or Firm*—Walter Katz

[57] ABSTRACT

An anti-microbial composition comprises an aqueous solution of a germicidal polymeric nitrogen compound and an oxidizing agent which potentiates the activity of the compound. The polymeric nitrogen compound includes a germicidal quaternary ammonium compound or a polyguanide compound. The oxidizing agent has a standard reduction potential between 0.85 and 2.0 volts, is soluble in water, non-toxic and enhances the activity germicidal of the nitrogen polymer at low concentrations. Suitable oxidizing agents include halogen oxides, oxyhalogens, halogens, and inorganic and organic peroxides.

23 Claims, No Drawings

ANTI-MICROBIAL COMPOSITIONS COMPRISING AN AQUEOUS SOLUTION OF A GERMICIDAL POLYMERIC NITROGEN COMPOUND AND A POTENTIATING OXIDIZING AGENT

CROSS-REFERENCE TO RELATED PATENT APPLICATIONS

This application is a continuation-in-part of Ser. No. 471,011, filed Mar. 1, 1983 now U.S. Pat. No. 4,499,077, which was a continuation of Ser. No. 231,257, filed Feb. 3, 1981 now abandoned by Richard F. Stockel and Murray Jelling.

BACKGROUND OF THE INVENTION

1. Field of the Invention

This application relates to anti-microbial compositions, and, more particularly, to improved disinfectant compositions for treatment of contact lenses and industrial materials.

2. Description of the Prior Art

Various compositions and methods are known for use in sterilization and cleaning of contact lenses, such as soft contact lenses, and for sanitization of industrial materials, such as water treatment systems. However, it is desired to provide new and improved anti-microbial compositions and methods of use which show an enhanced anti-microbial activity at low concentrations.

As stated by R. E. Phares in U.S. Pat. No. 3,689,673, sterilization of hydrophilic soft contact lenses may be carried out by soaking in an aqueous solution containing approximately 0.001–0.01% chlorhexidine for a time sufficient to sterilize the lens.

Various related methods are disclosed in other U.S. patents. U.S. Pat. No. 3,591,329 discloses the use of a cationic resin exchange material impregnated with active metallic silver. U.S. Pat. No. 3,755,561 teaches using an aqueous solution of polyvinyl pyrrolidone, a polyalkylene glycol and thimerosal. U.S. Pat. No. 3,873,696 discloses using a combination of potassium peroxymonosulfate in the presence of sodium chloride. In U.S. Pat. No. 3,876,768 is described the use of a chlorinated trisodium phosphate material which is similar to hypochlorite. U.S. Pat. No. 3,888,782 relates to the using of chlorhexidine and polyvinyl pyrrolidone. The use of an iodoform solution containing iodine, polyvinyl alcohol and boric acid is disclosed in U.S. Pat. No. 3,911,107. U.S. Pat. No. 3,912,450 proposes using a combination of an alcoholic glutaraldehyde solution containing a surfactant in conjunction with an ultrasonic radiation device.

U.S. Pat. No. 3,888,782 more particularly discloses an aqueous, substantially isotonic cleaning and sterilizing solution for plastic hydrophilic soft contact lenses containing, as active ingredients, chlorhexidine and polyvinylpyrrolidone. The solution is said to be non-toxic to the eye of the wearer of soft contact lenses and in the presence of a suitable amount of water soluble polyhydroxyethylmethacrylate to prevent the build-up of opaque deposits on the surfaces of soft contact lenses.

U.S. Pat. No. 4,029,817 discloses that soft contact lenses may be sterilized by contacting soft lenses with a sterile, aqueous, substantially isotonic solution containing as an active ingredient, an effective amount of a quaternary ammonium compound having the structural formula:

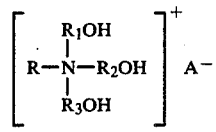

wherein R represents saturated or unsaturated alkyl residues of fatty acids and mixtures thereof containing from about 12–18 carbon atoms and preferably tallow, A is a non-toxic anion and $R_1$, $R_2$, and $R_3$ are the same or different and represent alkyl radicals having 1–3 carbon atoms; and together with a detoxifying amount of a non-toxic compound selected from the group consisting of water soluble polyhydroxyethyl methacrylate, carboxymethylcellulose, polyoxyethylene sorbitan fatty acids esters, polyoxyethylene alcohols, polyvinylpyrrolidone and mixtures thereof.

Many known quaternary ammonium compounds are generally good bactericides but are also irritating such as, for example, when they come into contact with the eye. Some of these compounds are moreover cationic and can be absorbed by porous surfaces and are difficult to remove. Where these compounds have been made less absorbent, they have never achieved the degree of perfection which would enable their use in critical applications such as with soft contact lenses.

Stabilized chlorine dioxide is known to be a powerful broad spectrum anti-microbial agent, effective in killing gram-positive and gram-negative bacteria, viruses, fungi, etc. The true composition of stabilized chlorine dioxide is an addition compound with the approximate formula of $2Na_2CO_3.3H_2O_2.ClO_2$. Stabilized chlorine dioxide has long been known as a much more effective anti-microbial agent than chlorine or hypochlorite. It completely consumes bacteria and other micro-organisms thereby preventing the formation of resistant strains. Although stabilized chlorine dioxide is a powerful oxidizing agent, its oxidation potential is less than that of hydrogen peroxide and it does not chlorinate organic compounds. It is purported to have 2.6 times the germicidal power of chlorine, yet it is 10 times as stable in aqueous solution. Stabilized chlorine dioxide is commercially available for a variety of industrial uses. However, it has never been used as an anti-microbial agent for soft contact lenses.

A 5% solution of stabilized chlorine dioxide is colorless, non-corrosive and easy to handle. It can be diluted to any concentration with water. It has government approval for many uses throughout the world. The product is inexpensive and has a long shelf life. The efficacy of stabilized chlorine dioxide increases as the pH value approaches the acid side. It does not have a characteristic chlorine-type odor. Stabilized chlorine dioxide has the unique property of oxygenation without chlorination. It destroys micro-organisms by reaction with cell structure and by speeding up the metabolism to the detriment of cell growth. It prevents immunity build-up. As it is infinitely soluble in water, any occluded chlorine dioxide that would occur within a soft lens could be readily removed by amply washing with distilled water or an isotonic solution. The oxidation potential for chlorine dioxide is $ClO_2 + 4H^+ + 5e^- = Cl^- + 2H_2O$ 1.50 volts. The oxidation potential for hydrogen peroxide is $H_2O_2 + 2H^+ + 2e^- = 2H_2O$ 1.77 volts.

Generally, U.S. Pat. No. 4,073,888 teaches the provision of a cold sterilization product for use on hard surfaces in hospitals, and kitchens, for medical instruments, and so forth. At the concentrations described, it is not, however, contemplated for use in disinfecting soft contact lenses, because (1) it would be irritating to the eye and (2) absorption of the quaternary salt in soft lenses would be a major problem.

More specifically, U.S. Pat. No. 4,073,888 relates to a composition of matter which is especially adapted for hard surface, cold sanitization and sterilization especially for killing spores and, more particularly, to aqueous compositions of matter containing chlorine dioxide and certain selected quaternary ammonium salts having the formula

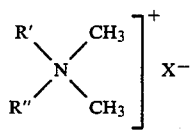

wherein R' and R" are alkyl radicals whose total carbon atoms number from 18 to 24, and preferably from 20–22. It is preferred that R' and R" be identical (symmetrical) but this is not necessary although each of the R' and R" radicals should have at least 8 carbon atoms. X is a chlorine, bromine, or any non-toxic non-interfering anion such as is known for the quaternary ammonium salts.

In order to prepare the composition of U.S. Pat. No. 4,073,888, the chlorine dioxide may be used either in pure form as well as a stabilized chlorine dioxide complex and in solution or suspension either aqueous or non-aqueous in concentrations of from 0.1% to 6.0%. It has been found, according to U.S. Pat. No. 4,073,888, generally necessary to employ one or more emulsifiers for the disclosed compositions. Those emulsifiers are generally linear compounds which are primary alcohol ethoxylates having 12 moles of ethylene oxide and the primary alcohol portion being derived from $C_{12}$–$C_{15}$. The optimum range for use in this composition is that the primary alcohol contains from 5 to 12 moles of ethylene oxide, but from 3 to 15 moles are useful. It is believed that the sporicidal activity of these compounds is enhanced by the use of alcohol which of course is not permissible for use in the cleaning of soft contact lenses.

U.S. Pat. No. 4,026,945 discloses synthetic antimicrobial quaternary ammonium copolymers. The copolymers are prepared by the condensation of at least two difunctional tertiary amines using a molar quantity of 1,4-dihalo-2-butene equal to the molar sum of the difunctional tertiary amines in the mixture. The product is disclosed as effective for the anti-microbial treatment of water but is not good for critical applications such as soft contact lenses as mentioned above.

One of the features of the copolymers of U.S. Pat. No. 4,026,945 is that the quaternary ammonium moieties are part of the long polymeric chain rather than being quaternary ammonium moieties on branches that are bonded to the polymeric chain. Another feature is that the copolymer is a unique reaction product and not a mere mechanical mixture of separate polymers. Therefore, the copolymers cannot be separated into constituent components, as would be the case if they were mere mechanical mixtures.

Another feature of U.S. Pat. No. 4,026,945 is that the primary chemical units comprising the polymeric chain are not identically repetitive as they would be if the product were an ordinary polymer. On the contrary, the several primary chemical units of the copolymer are randomly distributed in the polymeric chain.

U.S. Pat. No. 3,428,576 describes polymeric diguanides and their salts which have been found to be effective anti-microbial agents. These compounds are characterized by the recurring unit

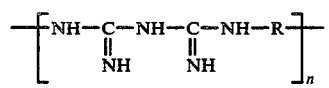

where R is a divalent radical, preferably an aliphatic hydrocarbon chain of 4 to 12 carbon atoms, and n is a number such that the molecular weight of the polydiguanide is at least about 800 and upwards to about 1200, and higher, and preferably from about 1,000 to about 5,000. Salts of these amino/imino polymeric compounds may be made with acids such as hydrochloric acid, sulfuric acid, acetic acid, gluconic acid, etc. A preferred product is the hydrochloric acid salt of poly(-hexamethylene diguanide). The product is commercially available from ICI Americas Inc. under the trade name IL-779. This product is an excellent anti-microbial agent, even in the presence of organic matter. It has a low order of toxicity and is chemically stable, non-corrosive, and odor-free. It is effective in concentrations as low as 0.001%.

In accordance with the above-described products, the required characteristics for an effective product are contained in positively-charged, nitrogen-containing cationic polymers, such as the quaternary ammonium compounds described in U.S. Pat. Nos. 4,026,945 and 4,027,020 and the amino and/or imino compounds and their salts, for example, the polydiguanides described in U.S. Pat. No. 3,428,576 as well as U.S. Pat. No. 2,643,232. These types of compounds having a plurality of cationic nitrogen species result in a more potent antimicrobial action, probably because of more points of interaction with the microbial cell wall. The other important factor is the higher molecular weight. The larger polymeric molecules are not as readily absorbed into the hydrophilic lens material as are the small monomeric molecules. For industrial applications, however, the molecular weight of the polymer is less significant.

Other oxidizing agents have been useful as disinfectants for industrial applications. For example, hydrogen peroxide is widely used as an antiseptic. It owes its action to its ready release of nascent oxygen with by product formation of water, but the effect is of short duration. Contrary to common belief, hydrogen peroxide is not decomposed instantly under usual conditions in acid solution unless its decomposition is catalyzed. Solutions of hydrogen peroxide also have poor power of penetration and are comparatively weak antiseptics. Therefore, there is an obvious need for expanding its biocidal spectrum and enhancing its duration of activity.

Hydrogen peroxide has been used also as a disinfectant for soft contact lenses; however in a 3.0 wt. percent solution only. In practice such solutions require the additional step of decomposing residual peroxide since any non-decomposed peroxide causes considerable damage to the easily oxidizable hydrophilic lenses polymer resulting in discoloration and changes in the visual acuity of the lenses.

In this invention, anti-microbial compositions containing polymeric germicides and peroxides such as hydrogen peroxide permit a surprisingly large reduction in the amount of the peroxide constituent while substantially increasing the activity of the composition. This provides a completely unexpected improvement in effectiveness-to-concentration characteristics of the compositions. For example, when combined with germicidal polymeric nitrogen compounds of the type described herein, peroxides can be used in such relatively low concentrations that the irritant effect of the peroxide is avoided.

SUMMARY OF THE INVENTION

What is provided herein are anti-microbial compositions comprising an aqueous solution of a germicidal polymeric nitrogen compound and an oxidizing agent which potentiates the activity of said compound at low concentrations. The oxidizing agent has a standard reduction potential of at least 0.85 volts but less than 2.0 volts, in which range it can oxidize the polymeric nitrogen compound at low concentrations in situ to form an oxidized nitrogen compound which possesses enhanced germicidal activity. The oxidizing agent used herein is soluble in water, non-toxic and, for use in contact lenses sterilization solutions, non-irritating to ocular tissue.

Suitable oxidizing agents which potentiate the activity of germicidal polymeric nitrogen compounds include halogenoxides, oxyhalogen acids and salts, halogens, halogen halides, inorganic and water soluble organic peroxides and permanganates, including chlorine dioxide, hypochlorites, chlorites, chlorates, perchlorates, hypobromites, bromates, chlorine, bromine, bromine chloride, hydrogen peroxide, persulfates, perborates, peracetic acid, t-butylhydroperoxide, percarbonates, peroxy acids and salts of molybdenum, tungsten and chromium and permanganates. Such oxidizing agents have the requisite characteristics for use herein, particularly (1) a standard reduction potential in the range of 0.85 and 2.0 volts, (2) solubility in water, and (3) non-toxic and non-irritating at low concentrations.

The polymeric germicide may be, for example, a quaternary ammonium compound or an amino and/or imino compound or salts thereof, and preferably one the size and shape of which is adapted to prevent the absorption thereof by porous surfaces such as characterizes the materials from which soft contact lenses are made. These components are used in solution in water.

In one preferred embodiment of the invention, the aforesaid quaternary ammonium compound is a copolymer of at least one difunctional tertiary amine and a dihalo organic compound such as, for example, 1,4-dihalo-2-butene. Monofunctional tertiary amines are also useful. Polydiguanides are an example of amino/imino compounds which can also be used in accordance with preferred embodiments of the invention.

The anti-microbial compositions of the present invention, when used as disinfectants for soft contact lenses, generally comprise about 0.001 to 0.05 weight percent of the germicidal polymer and 0.001 to 0.05 weight percent of the oxidizing agent. For industrial applications, such as biocidal treatment of water or sterilization of hospital rooms, the compositions are generally about 0.001 to 5.0 weight percent of each.

The pH of the composition generally is about 6.5 to 7.5 when used as a soft lens disinfectant, and about 5.5 to 8.5 for industrial applications.

DETAILED DESCRIPTION OF THE INVENTION

Table I below is a list of suitable oxidizing agents for use in the compositions of the invention. These oxidizing agents are water soluble, non-toxic, non-irritating and have a standard reduction potential of greater than 0.85 volts but less than 2.0 volts which potentiates the germicidal properties of the polymeric nitrogen compound.

TABLE I

| Halogen Oxides | |
|---|---|
| $ClO_2 + 4H^+ + 5e^- = Cl^- + 2H_2O$ | 1.50 v |
| Oxyhalogens | |
| $HClO + H_2O + 2e^- = Cl^- + H_2O$ | 1.49 v |
| $HClO_2 + 3H^+ + 3e^- = \frac{1}{2}Cl_2 + 2H_2O$ | 1.63 v |
| $ClO_3^- + 2H^+ + e^- = ClO_2 + H_2$ | 1.15 v |
| $ClO_4^- + 8H^+ + 8e^- = Cl^- + 3H_2O$ | 1.45 v |
| $HBrO + H^+ + e^- = \frac{1}{2}Br_2 + H_2O$ | 1.59 v |
| $HIO + H^+ + 2e^- = I^- + H_2O$ | 0.99 v |
| $ClO^- + H_2O + 2e^- = Cl^- + 2OH^-$ | 0.90 v |
| $IO_3^- + 6H^+ + 6e^- = I^- + 3H_2O$ | 1.09 v |
| $ClO_4^- + 8H^+ + 8e^- = Cl^- + 4H_2O$ | 1.37 v |
| $HBrO + H^+ + 2e^- = Br^- + H_2O$ | 1.33 v |
| $BrO_3^- = 6H^+ + 6e^- = Br^- + 3H_2O$ | 1.44 v |
| Halogens | |
| $Br_{2(aq)} + 2e^- = 2Br^-$ | 1.09 v |
| $Cl_{2(aq)} + 2e = 2Cl^-$ | 1.35 v |
| Peroxides | |
| $H_2O_2 + 2H^+ + 2e^- = H_2O$ | 1.78 v |
| Permanganate | |
| $MnO_4^- + 8H^+ - 8e = Mn^{2-} + 4H_2O$ | 1.49 v |

When the oxidizing agents are peroxides they include inorganic and water soluble organic peroxides such as have the general formula:

$$R-O-O-R^1$$

where
R=hydrogen, alkali or alkaline earth metal; and
$R^1$=hydrogen, alkali or alkaline earth metal, lower alkyl, acetyl, benzoyl, etc.

Peroxides generally have a standard reduction potential about the same as hydrogen peroxide (1.78 v) and thus are suitable for potentiating the germicidal activities of the polymeric nitrogen compound. While hydrogen peroxide is a preferred peroxide for use herein, other peroxides such as persulfates, peroxyacetic acids, perborates, percarbonates, lower alkyl hydroperoxides, and the peroxyacids or salts of molybdenum, tungsten or chromium, may be used as well.

Suitable germicidal polymeric nitrogen compounds and their preparation for use in the compositions of the invention are described below:

U.S. Pat. No. 4,026,945 discloses co-polymerization products made by condensing a mixture of two or more difunctional tertiary amines and a molar quantity of 1,4-dichloro-2-butene that is equal to the molar sum of the difunctional tertiary amines in the mixture. The difunctional tertiary amines are of the type

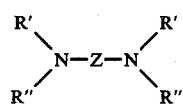

where Z consists of from one to three divalent aliphatic radicals of 2 to 10 carbon atoms which may contain 0 to 2 double bonds or 0 to 2 hydroxy substituents; wherein R' and R" are either the same or different and wherein they may be (a) primary or secondary alkyls having 1 to 20 carbon atoms, where the sum of the carbon atoms in R' and R" is no greater than 36, (b) hydroxy or dihydroxy derivatives of the aforesaid primary or secondary alkyls, (c) benzyl, (d) alkyl benzyl or (e) combined with N to form a heterocyclic group of either 5, 6, or 7 atoms.

All of the desired characteristics of the compounds of U.S. Pat. No. 4,026,945 are attained by causing a homogeneous mixture of solution of two or more difunctional tertiary amines to react with a molar quantity of 1,4-dichloro-2-butene which is equal to the molar sum of all of the components in the homogeneous mixture of solution of difunctional tertiary amines.

In this manner, if a homogeneous mixture or solution of 1,4-bis-(dimethylamino)-2-butene having the structure $(CH_3)_2-N-CH_2-CH=CH-CH_2-N-(CH_3)_2$ and N,N'-dimethyl piperazine having the structure

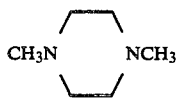

is reacted with a molar quantity of 1,4-dichloro-2-butene having the structure $Cl-CH_2-CH=CH-CH_2-Cl$ equal to the molar sum of the two difunctional tertiary amines, the two primary units which are part of the polymeric chain would be:

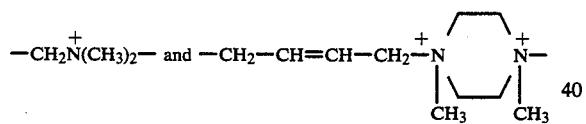

The ratio of the number of each of these units in the polymeric chain is very close to the molar ratio of the two difunctional tertiary amines in the starting mixture or solution, but the sequential order in which these two units appear in the polymeric chain is completely random, and therefore not identically repetitive.

The following examples are some of those given in U.S. Pat. No. 4,026,945.

EXAMPLE A 7.1 grams of 1,4-bis-(dimethylamino)-2-butene (0.05 mole) and 5.6 grams of diazabicyclo (2.2.2) octane (0.05 mole) are dissolved in 25 grams of water, and to the solution are added drop-wise 12.5 grams of 1,4-dichloro-2-butene (0.01 mole) at such a rate as to keep the temperature at about 60° C.–70° C. After addition is complete, and the exothermic reaction subsides, the mixture is heated in a steam bath for about 1 hour. The resulting solution contains about 50% by weight of active copolymer.

The same procedure can be repeated using as the mixtures of difunctional tertiary amines (a) 0.05 mole 1,4-bis-(morpholino)-2-butene and 0.05 mole of N,N'-dimethylpiperazine, (b) 0.05 mole of diazabicyclo (2.2.2) octane and 0.05 mole of 1,4-di-(N-homopiperidino)-2-butene, (c) 0.05 mole of 1,4-bis-(dimethylamino)-2-butene and 0.05 mole of N,N',N'-tetramethyl ethylenediamine. In each synthesis, the weight of water used as a solvent is approximately equal to the sum of the weights of the two difunctional tertiary amines and 1,4-dichloro-2-butene, so that the final mixture contains about 50% by weight of active copolymer.

EXAMPLE B 12.8 grams of 1,4-bis-(dimethylamino)-2-butene (0.09 moles) and 1.14 grams of N,N'-dimethyl piperazine (0.01 mole) are dissolved in 26 grams of water, and to the solution are added drop-wise 12.5 grams of 1,4-dichloro-2-butene at such a rate as to keep the temperature at about 60° C.–40° C. After addition is completed, and the exothermic reaction subsides, the mixture is heated in a steam bath for about 1 hour. The resulting solution contains about 50% weight of active copolymer.

The same procedure can be repeated using as the mixtures of difunctional tertiary amines (a) 0.08 mole of 1,4-bis-(dimethylamino)-2-butene and 0.02 mole of 1,4-bis-(N-morpholino)-2-butene, (b) 0.08 mole of 1,4-bis-(dimethylamino)-2-butene and 0.02 mole of 1,4-bis-(N-homopiperidino)-2-butene (c) 0.07 mole of 1,4-bis-(dimethylamino)-2-butene and 0.03 mole of 1,4-bis-(methyl dodecyl amino)-2-butene, and (d) 0.09 mole of 1,4-bis-(dimethylamino)-2-butene, and 0.01 mole of 1,4-bis-(methyl dodecylamino)-2-butene.

In each synthesis, the weight of the water used as a solvent is approximately equal to the sum of the weights of the two difunctional tertiary amines and 1,4-dichloro-2-butene, so that the final mixture contains about 50% by weight of active copolymer.

U.S. Pat. No. 4,027,020 describes other useful polymeric germicides in the form of anti-microbial polymeric quaternary ammonium compounds having linear chains which terminate in quaternary ammonium moieties, such compounds being formed by polymerization which is carried out in such a manner that the linear chains thereof are terminated in random fashion, the reaction resulting in the formation of the compounds being a one-step reaction between 1,4-dihalo-2-butene and a mixture of a difunctional tertiary amine and a monofunctional tertiary amine wherein the molar quantity of the difunctional amine is greater than the molar quantity of the monofunctional amine.

The following example from U.S. Pat. No. 4,027,020 exemplifies mono- and difunctional tertiary amines:

EXAMPLE C 28.4 grams of 1,4-bis-dimethylamino-2-butene (0.2 moles) and 1.40 grams of triethanolamine (0.01 moles) were dissolved in about 55.5 grams of water in a round-bottom flask fitted with a stirrer and reflux condenser, and 25.63 grams of 1,4-dichloro-2-butene (0.205 moles) were added slowly while the mixture was stirred. The reaction mixture was heated to 60°–70° C. and maintained at that temperature, with stirring, for about 6 hours. The reaction was 98% complete, as indicated by ionic chloride analysis. The residue contained about 50%, by weight, of active material.

It has now been found that combinations of oxidizing agents such as hydrogen peroxide and oxyhalogen compounds, on the one hand, and polymeric germicides, on the other hand, permit a surprisingly large reduction in the amounts of each of these constituents which must be used. This gives a completely unexpected improvement in effectiveness-to-concentration characteristics. As a consequence, many new uses for compositions containing these two constituents are envisaged.

For example, to obtain an effective anti-microbial agent based on stabilized chlorine dioxide alone, an amount of stabilized chlorine dioxide must be employed which would be irritating in ocular applications such as the treatment of soft contact lenses. When combined with the polymeric compounds mentioned above, such relatively low concentrations of stabilized chlorine dioxide may be used that the irritant effect is avoided.

In addition, polymeric compounds have a molecular weight of at least about 800 and upwards to about 12,000, and higher, and are preferably from about 1,000 to about 5,000 and have minimal absorbency in soft contact lens material. This feature insures that the polymeric compounds are not readily absorbed and thus do not tend to concentrate on or in the soft contact lenses, or subsequently on or in the ocular tissue, thereby further assuring against irritation. This result is moreover further amplified by the fact that only a minimal amount of the polymeric compound need be used.

Other polymeric compounds which may be used in accordance with the invention are shown by supplier and patent number below.

Millmaster Onyx Corp. patents referring to polymeric quaternary ammonium compounds having germicidal properties: U.S. Pat. Nos. 3,874,870; 3,923,973; 3,928,323; 3,929,990; 3,931,319; 4,001,432; 4,005,193; 4,012,446; 4,026,945; 4,027,020; 4,036,959; 4,055,712; 4,091,113.

ICI Americas Inc. patents referring to polymeric diguanides (polydiguanides) having germicidal properties: U.S. Pat. Nos. 2,643,232 and 3,428,576. Polymeric diguanides are compounds containing amino/imino groups and are positively-charged, nitrogen-containing, cationic compounds. Some specific compounds which may be used include polymeric hexamethylene diguanide and are represented by the formula:

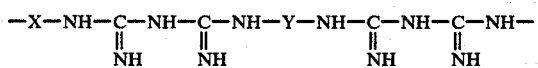

These substances can be manufactured by a process which comprises reacting a bisdicyanidiamide of the formula

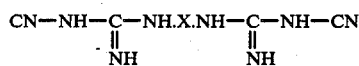

with a diamine of the formula

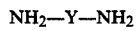

In one of its simplest forms, the invention merely involves immersing soft lenses (poly(2-hydroxyethylmethacrylate, slightly cross-linked) in a solution of a combination of Onamer M and stabilized chlorine dioxide. It is desirable to make the solution isotonic and for this purpose any of the well-known agents may be used. Preferably the pH of the solution is adjusted to about 4.5–8.5 and even more preferably to about 7.4 so that the lenses will be comfortable when inserted in the eyes. Other materials commonly used in contact lens solutions may also be employed such as buffering, chelating and thickening agents.

In order to test the effectiveness of the polymeric germicide, lenses were inoculated with various test organisms and then placed in solutions of various strengths of Onamer M and stabilized hydrogen peroxide. The maximum time to reach sterility for any of the organisms was recorded. The test organisms were: *Pseudomonas aeruginosa, Staphylococcus aureus, Escherichia coli* and *Candida albicans.*

The following results were obtained.

| | |
|---|---|
| 0.025% by wt. Onamer M | (U.S. Pat. No. 4,027,020, Ex. 2) |
| 0.025% by wt. hydrogen peroxide | 30 minutes |
| 0.009% by wt. Onamer M | (U.S. Pat. No. 4,027,020) |
| 0.008% by wt. hydrogen peroxide | <2 hours |

A further example illustrates the effectiveness of combining the hydrochloride salt of poly(hexamethylene diguanide) and hydrogen peroxide to reduce *Aspergillus niger* by 3 logs within 6 hours. I1-779 (available from ICI Americas Inc. and having a molecular weight of 1100–1300) is a twenty percent by weight aqueous solution of this salt.

| Disinfecting Solution | Microorganism | Control | 6 Hours |
|---|---|---|---|
| 0.005% polydiguanide 0.01% hydrogen peroxide | A. niger | $10^8$ org/ml | $10^5$ orgs/ml |

All germicides are aqueous solutions and it is simply required to weight out of the appropriate percentage by weight needed and dilute with sterile water. The solutions can contain 0.7% sodium chloride.

The following are exemplary concentrated formulations:

1.
Onamer M 0.05% by wt.
Hydrogen peroxide 0.05% by wt.
Boric acid 2% by wt.
Adjust to pH 7.0
Purified water Q.S. to make 100.00% by wt.

2.
Polydiguanide 0.05% by wt.
Sodium peroxide 0.5% by wt.
Boric acid 2% by wt.
Adjust to pH 7.0
Purified water Q.S. to make 100% by wt.

A solution containing stabilized chlorine dioxide and polydiguanide for use in sterilizing contact lenses of all types, including hydrophilic gel lenses, may be prepared from the following formulation containing other ingredients:

| | |
|---|---|
| Stabilized chlorine dioxide | 0.005% |
| Polydiguanide | 0.005% |
| Sodium chloride | 0.50% |
| Boric acid | 0.25% |
| Trisodium Edetate | 0.05% |
| Adjust to pH 7.0 | |
| Purified water Q.S. to make | 100.00% |

Other oxidizing agents whose half cell reduction potental is at least 0.85 volts or larger can be utilized provided they meet other safety, ocular irritation and stability criteria. Preferred oxidizing agents to be used in the invention are stabilized chlorine dioxide, hypochlorite, hydrogen peroxide and bromine chloride. The preferred range of these oxidizing agents is 0.001%–0.05% by weight in aqueous solution. The preferable range of this polymeric germicide is also 0.001%–0.05% by weight in aqueous solution. For industrial applications the oxidizing agent is present in an amount up to 5% by weight.

Other auxiliary components may be included in preparing applicable formulations as for example: additional anti-microbial agent, such as chlorhexidine, organic mercurials such as thimerosal and phenylmercuric acetate; surfactants, such as sodium borate; etc.

The following additional examples demonstrate the antimicrobial effect of solutions of the present invention. All concentrations are by weight in aqueous solutions similar to the above examples.

ADDITIONAL EXAMPLE I

Using replicate tests a solution containing 0.025% IL-779 and 0.025% sodium peroxide, there was obtained a reduction of $\geq 99.99\%$ against *Escherichia coli* ATCC #11229 within a 30 minute period.

A similar result was obtained utilizing 0.025% Onamer M and 0.025% peracetic acid.

ADDITIONAL EXAMPLE II

The anti-microbial effectiveness of the combination of IL-779, Onamer M and hydrogen peroxide was measured by a broth dilution method. The lowest concentration of this combination resulting in a complete inhibition of visible growth for 48 hours represents the minimum inhibition concentration (MIC) value. These values are intended to be used as an index of efficacy for preservative applications.

| Organism | Percent by Weight | MIC |
|---|---|---|
| Bacteria | | ppm (in which both agents are present in equal amounts) |
| *Escherichia coli* | 0.002% | 20 |
| *Pseudomonas aeruginosa* | 0.008% | 80 |
| *Streptococcus faecolis* | 0.001% | 10 |
| Fungi | | ppm (in which both agents are present in equal amounts) |
| *Aspergillus niger* | 0.04% | 400 |
| *Candida albicans* | 0.03% | 300 |
| *Saccharomyces turbidans* | 0.003% | 30 |

This data shows that this combination has broad spectrum activity against a wide variety of test organisms.

ADDITIONAL EXAMPLE III

This example illustrates the potentiation of antimicrobial activity with hydrogen peroxide on both Onamer M and IL-779 against *Serratia marcescens, Pseudomonas aeruginose,* and *Candida albicano* by D-value determination (D-value=time for reduction of inoculum by 90%.

| Organism ($10^6$ cells) | SOLUTION Onamer-M (.001 wt %) | Onamer-M (.001 wt %) hydrogen peroxide (.001 wt %) | IL-779 (.001 wt. %) Onamer-M (.001 wt %) hydrogen peroxide (.001 wt %) |
|---|---|---|---|
| *Serratia marcescens* ATCC 14041 | 4.8 hrs. | 1.2 hrs. | 30 min. |
| *Pseudomonas aeruginosa* ATCC 9027 | 1 hr. | 45 min | 15 min |
| *Candida albicans* ATCC 10231 | >24 hrs | >24 hrs. | 1.5 hrs. |

ADDITIONAL EXAMPLE IV

This example illustrates the industrial use of the compositions of the invention as a recirculating microbiological agent for cooling tower treatments against two pure cultures of bacteria. Percent kill of a composition of Onamer M and hydrogen peroxide against *Aerobacter aerogenes* and *Bacillus subtilis* ver. mycoides at pH7.

| CONCENTRATION (ppm of each component) | | | | |
|---|---|---|---|---|
| TIME(Hrs) | 5 | 10 | 25 | 50 |
| 1 | 99.0 | 99.9 | 100.0 | 100.0 |
| 2 | 100.0 | 100.0 | 100.0 | 100.0 |
| 3 | 100.0 | 100.0 | 100.0 | 100.0 |
| *Bacillus subtilis* ver. *mycoides* | | | | |
| 1 | 98.0 | 99.0 | 100.0 | 100.0 |

Two pure cultures of Algae Percent kill of Onamer M/polyhexamethylene biguanide/sodium percarbonate against *Chlorella vulgaris* and *Oscillatoria* sp. verus time and pH 7.0.

| CONCENTRATION (ppm of each component) | | | | | |
|---|---|---|---|---|---|
| TIME(hrs) | 50 | 60 | 80 | 90 | 100 |
| Chlorella Vulgaris | | | | | |
| 2 | 90.0 | 95.0 | 100.0 | 100.0 | 100.0 |
| 4 | 90.0 | 95.0 | 100.0 | 100.0 | 100.0 |
| 6 | 100.0 | 100.0 | 100.0 | 100.0 | 100.0 |
| Oscillatoria sp. | | | | | |
| 2 | 50.0 | 60.0 | 75.0 | 100.0 | 100.0 |
| 4 | 75.0 | 75.0 | 100.0 | 100.0 | 100.0 |
| 6 | 90.0 | 100.0 | 100.0 | 100.0 | 100.0 |

ADDITIONAL EXAMPLE V

ANTIMICROBIAL ACTIVITY OF SOLUTIONS OF ONAMER M OR IL-779 WITH AND WITHOUT ADDITION OF HYDROGEN PEROXIDE AFTER CONTACT TIMES OF 0.5, 3 AND 6 HOURS

| Test Compounds* (Percent Solids) | | Ratio Compound/ $H_2O_2$ | S. aureus ATCC #6538 | Str. faecalis ATCC #7080 | Ps. aeruginosa ATCC #15442 | E. Coli ATCC #15221 | C. Albicans ATCC #10231 | S. cerevesiae ATCC #560 |
|---|---|---|---|---|---|---|---|---|
| | | | EARLIEST DETECTED KILLING TIME, HOURS OF CONTACT | | | | | |
| Onamer M | | | | | | | | |
| 0.025% | 0.025% | 1/1 | <0.5 | <0.5 | <0.5 | <0.5 | <0.5 | <0.5 |
| | 0.000% | 1/0 | <0.5 | 3 | <0.5 | <0.5 | <0.5 | 3 |
| 0.01% | 0.01% | 1/1 | <0.5 | <0.5 | <0.5 | <0.5 | <0.5 | <0.5 |
| | 0.005% | 2/1 | <0.5 | <0.5 | <0.5 | <0.5 | <0.5 | <0.5 |
| | 0.00 | 1/0 | <0.5 | 3 | <0.5 | <0.5 | <0.5 | 3 |
| IL-779 | | | | | | | | |

ADDITIONAL EXAMPLE V-continued

ANTIMICROBIAL ACTIVITY OF SOLUTIONS OF ONAMER M OR IL-779 WITH AND WITHOUT ADDITION OF HYDROGEN PEROXIDE AFTER CONTACT TIMES OF 0.5, 3 AND 6 HOURS

| Test Compounds* (Percent Solids) | | Ratio Compound/ $H_2O_2$ | S. aureus ATCC #6538 | Str. faecalis ATCC #7080 | Ps. aeruginosa ATCC #15442 | E. Coli ATCC #15221 | C. Albicans ATCC #10231 | S. cerevesiae ATCC #560 |
|---|---|---|---|---|---|---|---|---|
| | $H_2O_2$ | | | | EARLIEST DETECTED KILLING TIME, HOURS OF CONTACT | | | |
| 0.025% | 0.025% | 1/1 | <0.5 | <0.5 | <0.5 | <0.5 | <0.5 | <0.5 |
| | 0.000% | 1/0 | <0.5 | <0.5 | <0.5 | <0.5 | <0.5 | <0.5 |
| 0.01% | 0.01% | 1/1 | <0.5 | <0.5 | <0.5 | <0.5 | <0.5 | <0.5 |
| | 0.005% | 2/1 | <0.5 | <0.5 | <0.5 | <0.5 | <0.5 | <0.5 |
| | 0.00% | 1/0 | <0.5 | <0.5 | <0.5 | <0.5 | <0.5 | 3 |
| $H_2O_2$ ONLY | 0.025% | | 3 | >6 | 6 | 6 | >6 | >6 |
| | 0.01% | | 3 | >6 | 6 | 6 | >6 | >6 |
| | 0.005% | | 6 | >6 | 6 | >6 | >6 | >6 |

*Concentrations based on percent solids content of original solutions

While the mechanism of potentiation of the biocidal activity of germicidal polymeric nitrogen compounds used in the aqueous composition of the invention is not completely understood at present, it is believed that these germicidal nitrogen polymers oxidize in situ at an N—H bond or at the alpha hydrogen in the R—$CH_2$—N group to produce small amounts of low molecular weight components such as aldehydes which are themselves excellent germicides. These aldehydes may be produced, for example, through a halogen oxidation to produce an —NX intermediate which in aqueous solution generates the aldehyde, or by direct oxidation of an alpha $CH_2$ group to provide the aldehyde. In both cases, an oxidizing agent having a standard reduction potential of at least 0.85 volts and less than 2.0 volts has sufficient strength to effect the desired oxidation of such nitrogen polymers without decomposing the polymer. Furthermore, as organisms are being killed by the antimicrobial composition, oxidation of polymer can continue in situ to generate more of the highly active oxidization product.

What is claimed is:

1. An anti-microbial composition comprising an aqueous solution of:
   (1) 0.001 to 0.05 percent by weight of a germicidal polymer selected from the group consisting of:
      (a) an anti-microbial polymeric quaternary ammonium compound made by condensing a difunctional tertiary amine, or a mixture of two or more difunctional tertiary amines, and a molar quantity of 1,4-dichloro-2-butene that is equal to the moles of said difunctional tertiary amine or the molar sum of the difunctional tertiary amines in the mixture, the difunctional tertiary amines being of the type

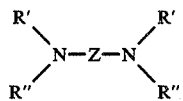

where Z consists of from one to three divalent aliphatic radicals of 2 to 10 carbon atoms which may contain 0 to 2 double bonds or 0 to 2 hydroxy substituents, wherein R' and R" are either the same of different and wherein they be (i) primary or secondary alkyls having 1 to 20 carbon atoms, where the sum of the carbon atoms in R' and R" is no greater than 36, (ii) hydroxy or dihydroxy derivatives of the aforesaid primary or secondary alkyls, (iii) benzyl, (iv) alkyl benzyl or (v) combined with N to form a heterocyclic group of either 5, 6, or 7 atoms; or said difunctional tertiary amines and a monofunctional tertiary condensed amine with 1,4-dichloro-2-butene wherein the molar quantity of the difunctional tertiary amine is greater than the molar quantity of the monofunctional tertiary amine, and,
      (b) a polydiguanide; and,
   (2) 0.001 to 0.05 percent by weight of an oxidizing agent which has a standard reduction potential in the range defined by that of hydrogen peroxide, chlorine dioxide and hypochlorite, is soluble in water, non-toxic and, in said compositions, enhances the activity of said compound by oxidation in situ at low concentrations.

2. An anti-microbial composition according to claim 1, wherein said oxidizing agent includes halogen oxides, oxyhalogens, halogens, inorganic and organic peroxides and permanganate.

3. An anti-microbial composition according to claim 2, wherein said inorganic and organic peroxides includes hydrogen peroxide, persulfates, peroxyacetic acid, perborates, percarbonates, lower alkylhydroperoxides and the peroxy acids or salts of molybdenum, or tungsten.

4. An anti-microbial composition according to claim 1, wherein said oxidizing agent is hydrogen peroxide.

5. An anti-microbial composition according to claim 1, wherein the pH of said composition is about 5.5 to 8.5.

6. An anti-microbial compositions according to claim 1, wherein the pH of said composition is about 6.5 to 7.5.

7. An anti-microbial composition according to claim 1 in which said polymeric compound is polymeric hexamethylene diguanide.

8. An anti-microbial composition according to claim 1, wherein said polymeric quaternary ammonium compound is made by condensing a difunctional tertiary amine with a molar equivalent quantity of 1,4-dichloro-2-butene.

9. An anti-microbial composition according to claim 1, wherein said polymeric quaternary ammonium compound is made by condensing a mixture of two or more difunctional tertiary amines and a molar equivalent equal to their sum of 1,4-dichloro-2-butene.

10. An anti-microbial composition according to claim 1, wherein said polymeric quaternary ammonium compound is made by condensing a mixture of a difunctional amine and a monofunctional tertiary amine, wherein the molar quantity of the difunctional amine is greater than the molar quantity of the monofunctional amine, with 1,4-dichloro-2-butene.

11. An anti-microbial composition according to claim 8, wherein said oxidizing agent is hydrogen peroxide.

12. An anti-microbial composition according to claim 8 wherein said oxidizing agent is stabilized chlorine dioxide.

13. An anti-microbial composition according to claim 9 wherein said oxidizing agent is hydrogen peroxide.

14. An anti-microbial composition according to claim 10 wherein said oxidizing agent is hydrogen peroxide.

15. An anti-microbial composition according to claim 10 wherein said oxidizing agent is stabilized chlorine dioxide.

16. An anti-microbial composition according to claim 1 wherein said oxidizing agent is stabilized chlorine dioxide.

17. An anti-microbial composition according to claim 1 wherein said anti-microbial polymeric quaternary ammonium compound is Onamer M.

18. An anti-microbial composition according to claim 17, wherein said oxidizing agent is hydrogen peroxide.

19. An anti-microbial composition according to claim 17 wherein said oxidizing agent is stabilized chlorine dioxide.

20. A method of treating industrial materials such as the biocidal treatment of water and the sterilization of hospital rooms, which comprises contacting the same with an antimicrobial composition comprising an aqueous solution of:

(1) 0.001 to 5 percent by weight of germicidal polymer selected from the group consisting of:

(a) an anti-microbial polymeric quaternary ammonium compound made by condensing a difunctional tertiary amine, or a mixture of two or more difunctional tertiary amines, and a molar quantity of 1,4-dichloro-2-butene that is equal to the moles of said difunctional tertiary amine or the molar sum of the difunctional tertiary amines in the mixture, the difunctional tertiary amines being of the type

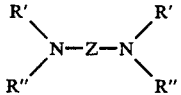

where Z consists of from one to three divalent aliphatic radicals of 2 to 10 carbon atoms which may contain 0 to 2 double bonds or 0 to 2 hydroxy substituents, wherein R' and R" are either the same of different and wherein they be (i) primary or secondary alkyls having 1 to 20 carbon atoms, where the sum of the carbon atoms in R' and R" are is no greater than 36, (ii) hydroxy or dihydroxy derivatives of the aforesaid primary or secondary alkyls, (iii) benzyl, (iv) alkyl benzyl or (v) combined with N to form a heterocyclic group of either 5, 6 or 7 atoms; or said difunctional tertiary amines and a monofunctional tertiary amine condensed with 1,4-dichloro-2-butene wherein the molar quantity of the difunctional tertiary amine is greater than the molar quantity of the monofunctional tertiary amine, and, (b) a polydiguanide; and, (2) 0.001 to 5 percent by weight of an oxidizing agent which has a standard reduction potential in the range defined by that of hydrogen peroxide, chlorine dioxide and hypochlorite, is soluble in water, non-toxic and, in said compositions, enhances the activity of said compound by oxidation in situ at low concentrations.

21. A method according to claim 20 in which the polymeric compound is polymeric hexamethylene diguanide.

22. A method of treating soft contact lenses by contacting the same with an antimicrobial composition comprising an aqueous solution of:

(1) 0.001 to 0.05 percent by weight of germicidal polymer selected from the group consisting of:

(a) an anti-microbial polymeric quaternary ammonium compound made by condensing a difunctional tertiary amine, or a mixture of two or more difunctional tertiary amines, and a molar quantity of 1,4-dichloro-2-butene than is equal to the moles of said difunctional tertiary amine or the molar sum of the difunctional tertiary amines in the mixture, the difunctional tertiary amines being of the type

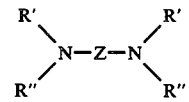

where Z consists of from one to three divalent aliphatic radicals of 2 to 10 carbon atoms which may contain 0 to 2 double bonds or 0 to 2 hydroxy substituents, wherein R' and R" are either the same of different and wherein they be (i) primary or secondary alkyls having 1 to 20 carbon atoms, where the sum of the carbon atoms in R' and R" are is no greater than 36, (ii) hydroxy or dihydroxy derivatives of the aforesaid primary or secondary alkyls, (iii) benzyl, (iv) alkyl benzyl or (v) combined with N to form a heterocyclic group of either 5, 6 or 7 atoms; or said difunctional tertiary amines and a monofunctional tertiary amine condensed with 1,4-dichloro-2-butene wherein the molar quantity of the difunctional tertiary amine is greater than the molar quantity of the monofunctional tertiary amine, and, (b) a polydiguanide; and, (2) 0.001 to 0.05 percent by weight of an oxidizing agent which has a standard reduction potential in the range defined by that of hydrogen peroxide, chlorine dioxide and hypochlorite, is soluble in water, non-toxic and, in said compositions, enhances the activity of said compound by oxidation in situ at low concentrations.

23. A method according to claim 22 in which the polymeric compound is polymeric hexamethylene diguanide.

* * * * *